United States Patent [19]
Fegley et al.

[11] Patent Number: 5,546,183
[45] Date of Patent: Aug. 13, 1996

[54] LIDAR DROPLET SIZE MONITOR FOR IN-FLIGHT MEASUREMENT OF AIRCRAFT ENGINE EXHAUST CONTRAILS, DROPLETS AND AEROSOLS

[75] Inventors: Ronald W. Fegley, Whittier; Darrell A. Terry, Huntington Beach, both of Calif.

[73] Assignee: Northrop Grumman Corporation, Los Angeles, Calif.

[21] Appl. No.: 321,715

[22] Filed: Oct. 12, 1994

[51] Int. Cl.$^6$ ............................................. G01C 3/00
[52] U.S. Cl. ................................. 356/336; 356/342
[58] Field of Search ................................. 356/336, 342

[56] References Cited

U.S. PATENT DOCUMENTS

| | | | |
|---|---|---|---|
| 4,251,733 | 2/1981 | Hirleman, Jr. | 250/575 |
| 4,459,024 | 7/1984 | Gergely | 356/342 |
| 4,492,467 | 1/1985 | Drain et al. | 356/336 |
| 4,497,577 | 2/1985 | Sato et al. | 356/336 |
| 4,871,251 | 10/1989 | Preikschat et al. | 356/336 |
| 5,047,653 | 9/1991 | Garcia et al. | 250/574 |
| 5,094,532 | 3/1992 | Trainer et al. | 356/336 |
| 5,116,124 | 5/1992 | Huttmann | 356/342 |
| 5,206,698 | 4/1993 | Werner et al. | 356/5 |
| 5,285,256 | 2/1994 | Nelson et al. | 356/342 |

OTHER PUBLICATIONS

Klett, James D. "Stable analytical inversion solution for processing ledar returns", *Applied Optics*, vol. 20, No. 2. (15 Jan. 1981) pp. 211–220.

*Primary Examiner*—Richard A. Rosenberger
*Attorney, Agent, or Firm*—Terry J. Anderson; Karl J. Hoch, Jr.

[57] ABSTRACT

A lidar system which utilizes optical backscatter and extinction to determine the size of particles inside the exhaust plume of an aircraft at a distance of several hundred meters behind the aircraft. The system transmits a laser beam through the exhaust plume of the aircraft, where it is reflected by the particles contained in the exhaust plume. The reflected light is detected by a receiver, where it is processed by a computer to calculate the size of the particles in the exhaust plume.

8 Claims, 3 Drawing Sheets

LIDAR DROPLET SIZE MONITOR FOR IN-FLIGHT MEASUREMENT OF AIRCRAFT ENGINE EXHAUST CONTRAILS, DROPLETS AND AEROSOLS

GOVERNMENT LICENSE RIGHTS

The U.S. Government has a paid up license in this invention and the right in limited circumstances to require the patent owner to license others on reasonable terms as provided for by the terms of contract number F33657-81-C-0067 awarded by the United States Air Force.

FIELD OF THE INVENTION

The invention relates generally to the field of optical radar devices, and particularly to lidar droplet size monitors for in-flight measurement of aircraft engine exhaust contrails, droplets and aerosols.

BACKGROUND OF THE INVENTION

The term lidar is an acronym for light detection and ranging. Lidar systems employ intense pulses of light, typically generated by lasers, and large telescopes and sensitive optical detectors to receive the reflected pulses. They are most commonly used to measure the composition and structure of the atmosphere, such as by tracking weather balloons, smoke puffs, reflections and scattering effects of clouds, and rocket trails. The very narrow beam width, narrow line width, and ultra short pulses of the laser make it possible to optically probe the atmosphere with exceptional sensitivity and resolution.

A contrail or condensation trail is the visible trail of condensed water vapor or ice particles left behind an aircraft, an airfoil, etc. in motion through the air. There are three kinds of condensation trails or vapor trails: the aerodynamic type, caused by reduced pressure of the air in certain areas as it flows past the aircraft; the convection type, caused by the rising of air warmed by an engine; and the engine-exhaust, or exhaust moisture, type, formed by the ejection of water vapor from an engine into a cold atmosphere.

Lidar systems have been used to measure the particles that comprise contrails. The foregoing is accomplished by measuring the optical backscatter of the particles in a portion of the contrail.

Systems have been installed in aircraft to measure the optical characteristics of the atmosphere in a region near the airplane. However, optical techniques have not been utilized to measure the exhaust plume or contrail region near an airplane in flight.

Prior art device did not permit a pilot to monitor the size of the particles inside his exhaust plume at a distance of several hundred meters behind his airplane. Thus, one of the disadvantages of the prior art was that the pilot was unable to monitor the size of soot particles, etc. in the exhaust plume or contrails to minimize pollution emissions of the jet engines of the aircraft.

Another disadvantage of the prior art was that the pilot was unable to monitor the size of particles in the exhaust plume or contrail to more efficiently use the engines of the aircraft.

Reference may be had to the following patents for further information concerning the state of the prior art.

In U.S. Pat. No. 4,251,733, issued Feb. 17, 1981, entitled "Technique for Simultaneous Particle Size and Velocity Measurement" to Hirleman, Jr. there is disclosed the analysis of backscattered light from a laser source for purposes of simultaneously determining particle size and velocity.

In U.S. Pat. No. 4,492,467, issued Jan. 8, 1985 entitled "Measurement of The Size of Particles" to Drain et al. there is disclosed a method of determining the size of spherical particles by detecting backscattered light from a laser source.

In U.S. Pat. No. 4,497,577, issued Feb. 5, 1985 "Steam Wetness Measuring Apparatus" to Sato et al. there is disclosed a steam wetness measuring apparatus wherein information derived from backscattered light is processed to determine the particle size distribution of the water droplets.

In U.S. Pat. No. 4,871,251, issued Oct. 3, 1989 entitled "Apparatus And Method For Particle Analysis" to Preikschat et al. there is disclosed an apparatus and method for analyzing the size and number of particles in a fluent medium using backscattered light from a laser light source.

In U.S. Pat. No. 5,047,653, issued Sep. 10, 1991 entitled "Device On Board A Moving Vehicle To Obtain Signals Representative Of The Relative Speed of The Vehicle With Respect To An Ambient Fluid" to Garcia et al. there is disclosed an apparatus which is mounted on an aircraft that determines the relative speed of the aircraft with respect to an ambient fluid by measuring the light reflected by particles moving through a measuring volume of the ambient fluid.

In U.S. Pat. No. 5,094,532, issued Mar. 10, 1992 entitled "Method And Apparatus For Measuring Small Particle Size Distribution" to Trainer et al. there is disclosed a method of measuring size and distribution of moving particles within a scattering medium by comparing the frequency of the scattered light to the nonscattered light.

In U.S. Pat. No. 5,116,124 issued May 26, 1992 entitled "Measurement System For Scattering of Light" to Huttmann there is disclosed an apparatus using backscattering laser light for the measurement of atmospheric visibility or optical density. The apparatus may be mobile by being used in vehicles.

In U.S. Pat. No. 5,206,698 issued Apr. 27, 1993, entitled "Lidar Arrangement For Measuring Atmospheric Turbidities" to Werner et al. there is disclosed a lidar arrangement for measuring atmospheric turbidities wherein a signal processing unit distinguishes between different kinds of visibility obstacles such as fog, rain, snow or solid obstacles. The arrangement may be made mobile.

SUMMARY OF THE INVENTION

The present invention overcomes the disadvantages of the prior art by providing a lidar system that utilizes optical backscatter and extinction to permit a pilot to monitor the size of the particles inside his exhaust plume or contrail at a distance of several hundred meters behind his airplane. Thus, an advantage of this invention is that the pilot is able to monitor the size of soot particles, etc. in the exhaust plume to minimize pollution emissions of the jet engines of the aircraft.

An additional advantage of this invention is that the pilot is able to monitor particle sizes in the exhaust plume or contrail in order to improve airplane engine performance.

DESCRIPTION OF THE PREFERRED EMBODIMENTS

Figure 1:
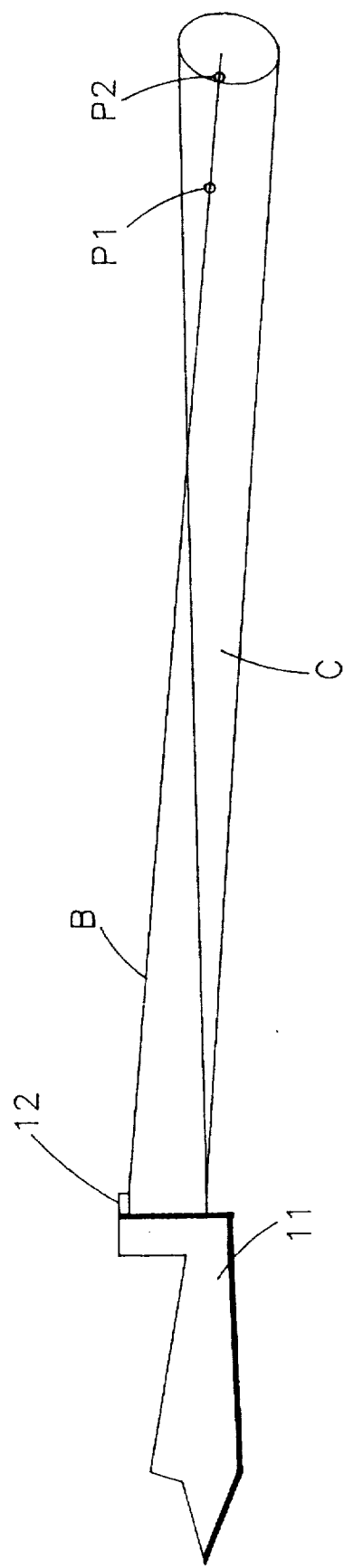
FIG. 1 is a drawing of the geometry of two points P1 and P2 that exist within a exhaust plume or contrail.

Referring now to the drawings in detail, and more particularly to FIG. 1, the reference character 11 represents an aircraft that is flying. Aircraft 11 has affixed thereto the apparatus of this invention 12. The apparatus of this invention 12 determines the average particle size between two points P1 and P2 in an aircraft engine exhaust, C. Apparatus 12 transmits a beam B, of laser light to the exhaust plume, C. Point P1 is located at an arbitrary point in the region where beam B passes through exhaust plume C and point P2 is located inside exhaust plume C at a distance from aircraft 11 further than point P1. The beam of laser light B is then reflected back from the exhaust plume C and is collected by a receiver hereinafter described, that is contained within apparatus 12.

Figure 2:
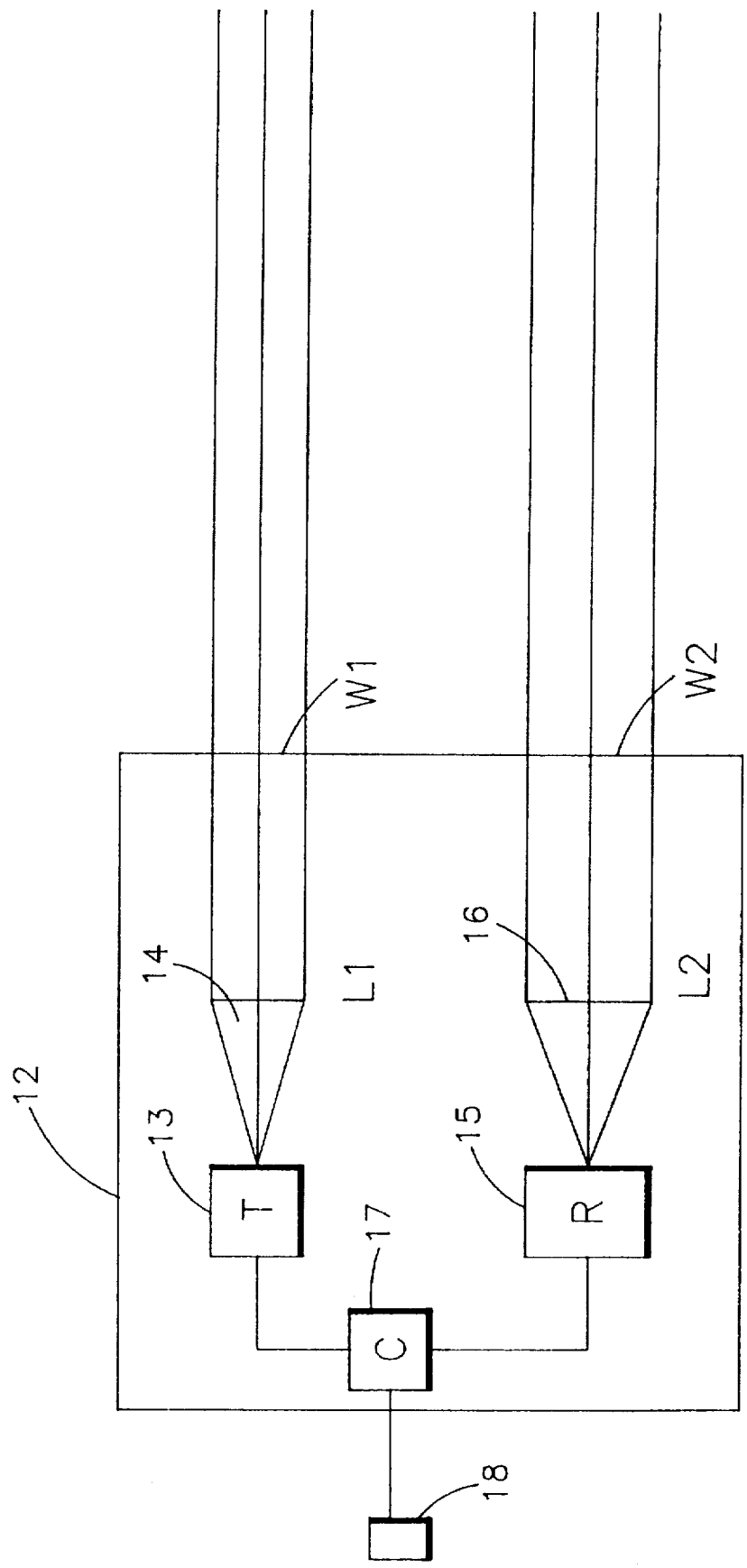
FIG. 2 is a block diagram of the apparatus of this invention.

FIG. 2 is a block diagram of the apparatus of this invention 12. Apparatus 12 comprises a laser transmitter 13; a lens 14; a window W1; a receiver 15; a lens 16; a window W2 and a computer 17. Laser transmitter 13, transmits a beam of light that propagates through lens 14 and window W1. Laser transmitter 30 has a wavelength chosen in the range between 0.2 and 25.0 micrometers. The wavelength is optimized for the particular application. The aforementioned beam of light travels out to exhaust plume C (described in the description of FIG. 1), where it is reflected by the particles in the exhaust plume. The reflected light passes through window W2, and lens 16. The reflected light is now detected by receiver 15. Receiver 15 transmits the reflected light to computer 17. Computer 17 process the detected light by utilizing a method disclosed by James Klett in Applied Optics, Jan. 15, 1981, p. 211, which is herein incorporated by reference to determine the droplet size. James Klett's method will be described in the description of FIG. 3.

Figure 3:
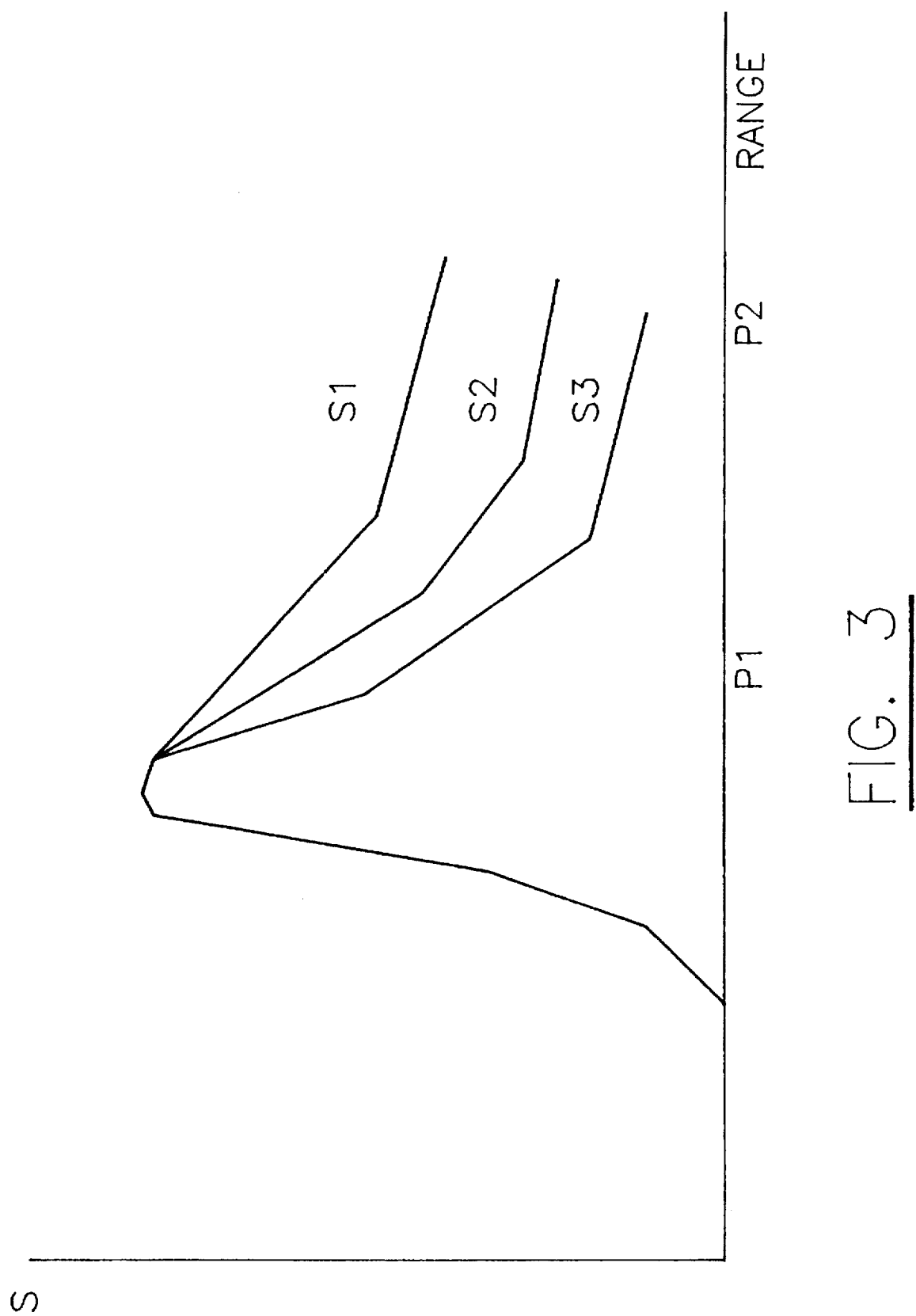
FIG. 3 is a graph of the data that is received from the apparatus of the invention.

FIG. 3 is a graph of the signal transmitted by receiver 15 to computer 17 vs. the range of particles P1 and P2 from airplane 11. The signal transmitted by receiver 15 consists of a range resolved radar return, S. The signal strength of the signal S, is dependent upon the distance between apparatus 12 as well as the types of material that beam B (FIG. 1) passes through. Signal S, will be attenuated if beam B contacts any particles.

Three signals are illustrated in FIG. 3, S1, S2, and S3. The signals S1, S2, and S3 all become strong at P1, an arbitrary point in the region where beam B passes through exhaust plume C. Point P2 is located at an arbitrary point inside exhaust plume C at a distance from aircraft 11 further than point P1. If exhaust plume C is strongly attenuating, the signal would look like S3, i.e., there is little signal returned from P2. If exhaust plume C is weakly attenuating, the signal would look like S1, i.e., there is strong signal returned from P2. When exhaust plume C is moderately attenuating, the signal would look like S1, i.e., there is a moderate strength signal returned from P2.

The degree of attenuation of signal S, depends on the size of the particles in exhaust plume C. Computer 17 uses a method developed by James Klett in Applied Optics, Jan. 15, 1981, p. 211, which is incorporated by reference to determine the droplet size. It is based on measuring the optical extinction of the light beam (how much of the light beam is removed for each unit of distance traveled inside the plume) and the optical backscatter of the light beam (how much of the light is backscattered for each unit of distance traveled inside the plume.

The ratio of the optical extinction to the optical backscatter will uniquely determine the droplet size, when the basic droplet characteristics are known (type of material, rough range of sizes to be expected).

Computer 17 digitizes the return signal, determines the above parameters, and assigns a droplet size to the particles in exhaust plume C, based upon that determination.

Computer 17 transmits the determined particle sizes to display 18. The pilot views display 18 and notes the determined particle size to change the mixture of fuel being burned by the aircraft engines to reduce pollution and make the engines more efficient. Display 18 may be a needle type panel meter which points to the droplet size, or any similar device known to one skilled in the art.

We claim:

1. A lidar system that is aboard a flying vehicle to monitor a particle size of particles contained in an exhaust plume produced by the vehicle, said system comprising:

means for propagating a beam that travels through the exhaust plume;

means for detecting the propagated beam after the propagated beam is reflected by the particles contained in the exhaust plume; and means coupled to said detecting means for calculating the particle size of the particles contained in the exhaust plume.

2. The system claimed in claim 1, further including means coupled to said calculating means for displaying the particle size of the particles contained in the exhaust plume.

3. The system claimed in claim 2, wherein said displaying means is a meter.

4. The system claimed in claim 1, wherein said propagating means is a laser.

5. The system claimed in claim 4, wherein said propagating means further includes:

a lens positioned between the laser and the propagated beam, said lens focusing the propagated beam.

6. The system claimed in claim 1, wherein said detecting means is a receiver.

7. The system claimed in claim 6, wherein said detecting means further includes a lens that is positioned between the reflected propagated beam and said receiver, said lens focusing the reflected propagated beam.

8. The system claimed in claim 1, wherein said calculating means is a computer.

* * * * *